(12) United States Patent
Hisano et al.

(10) Patent No.: US 9,025,852 B2
(45) Date of Patent: May 5, 2015

(54) SUBSTRATE INSPECTION APPARATUS AND METHOD FOR OPERATING THE SAME

(75) Inventors: Kazuya Hisano, Koshi (JP); Hiroshi Tomita, Koshi (JP); Norihisa Koga, Koshi (JP); Tadashi Nishiyama, Koshi (JP); Makoto Hayakawa, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 392 days.

(21) Appl. No.: 13/482,270

(22) Filed: May 29, 2012

(65) Prior Publication Data

US 2012/0307045 A1 Dec. 6, 2012

(30) Foreign Application Priority Data

May 30, 2011 (JP) ................................. 2011-120917

(51) Int. Cl.
| | |
|---|---|
| *G06K 9/00* | (2006.01) |
| *G01N 21/956* | (2006.01) |
| *G01N 21/88* | (2006.01) |
| *G01N 21/93* | (2006.01) |
| *G01N 21/95* | (2006.01) |
| *G06T 7/00* | (2006.01) |

(52) U.S. Cl.
CPC ............ *G01N 21/956* (2013.01); *G06T 7/0004* (2013.01); *G01N 21/8806* (2013.01); *G01N 21/93* (2013.01); *G01N 21/9501* (2013.01); *G01N 2021/9513* (2013.01)

(58) Field of Classification Search
CPC ...... G01N 21/93; G01N 21/956; H01L 21/66; H04N 7/18
See application file for complete search history.

(56) References Cited

U.S. PATENT DOCUMENTS

| | | | | |
|---|---|---|---|---|
| 6,456,373 | B1 * | 9/2002 | Wienecke et al. | 356/218 |
| 6,842,220 | B1 * | 1/2005 | Dishon et al. | 355/27 |
| 8,774,491 | B2 * | 7/2014 | Seki et al. | 382/144 |
| 2011/0216312 | A1 * | 9/2011 | Matsumoto et al. | 356/237.1 |

FOREIGN PATENT DOCUMENTS

| | | | | |
|---|---|---|---|---|
| JP | 05-215696 | A1 | 8/1993 | |
| JP | 05215696 | A * | 8/1993 | ............ G01N 21/88 |
| JP | 08-152311 | A1 | 6/1996 | |
| JP | 2001-20143 1 | A1 | 7/2001 | |
| JP | 2002-141274 | A1 | 5/2002 | |

OTHER PUBLICATIONS

Japanese Office Action (Application No. 2011-120917) dated Dec. 17, 2013.

* cited by examiner

*Primary Examiner* — Thai Tran
*Assistant Examiner* — Christopher T. Braniff
(74) *Attorney, Agent, or Firm* — Burr & Brown, PLLC

(57) ABSTRACT

In one embodiment, a substrate inspection apparatus performs, in its maintenance mode, operations including: guiding a light emitted from an illuminating unit to an imaging device via a light-guiding member disposed in a casing; judging whether or not a level of a brightness signal obtained by the imaging device falls within a predetermined allowable range when a light emitted from the illuminating unit falls on the imaging device via the light-guiding member; and alarming, if it is judged that the value of the brightness signal is out of the predetermined allowable range, that replacement of the illuminating unit is required.

20 Claims, 14 Drawing Sheets

SUBSTRATE INSPECTION APPARATUS AND METHOD FOR OPERATING THE SAME

CROSS-REFERENCE TO RELATED APPLICATION

This application is based on and claims the benefit of priorities from Japanese Patent Application No. 2011-120917 filed on May 30, 2011, the entire contents of which are incorporated herein by reference.

BACKGROUND OF THE INVENTION

1. Field of the Invention

The present disclosure relates to a substrate inspection apparatus that picks up an image of a substrate, such as a semiconductor wafer and an LCD substrate (a glass substrate for a liquid crystal display unit) so as to perform inspection of the substrate, and also relates to a method for operating the same.

2. Description of Related Art

In manufacturing of semiconductor devices, photolithographic processes, including a coating process that applies a resist solution to a semiconductor wafer (hereinafter referred to simply as "wafer") to form a resist film, an exposure process that exposes the resist film with a predetermined pattern, and a developing process that develops the exposed resist film, are sequentially performed, so that a patterned resist film is formed on the wafer.

The wafer having experienced the photolithographic processes is loaded into a substrate inspection apparatus, which is disposed in a coating and developing system that performs the resist coating process and the developing process. Then, the surface of the wafer is imaged by a camera provided in the inspection apparatus, and the image of the wafer is displayed on an output screen. Based on the displayed image, there are performed inspection for inspecting whether or not the resist film is properly formed on the surface of the wafer, and inspection for inspecting whether or not the surface of the wafer has scratches and/or foreign matters adhered thereto.

Upon imaging, the wafer is illuminated by an illuminating unit provided in the substrate inspection apparatus. The illuminance of the illuminating unit gradually decreases by deterioration over time. When the wafer is imaged under a decreased illuminance, precision of inspection is reduced. Thus, periodic maintenance of the substrate inspection apparatus is performed. In some cases, an inspection wafer (i.e., a wafer exclusively for inspection or maintenance of the inspection apparatus) having thereon no film (e.g., a resist film) is loaded into the substrate inspection apparatus, and the illuminance of the illuminating unit is inspected based on an image obtained by imaging the inspection wafer. If it is judged that the illuminance of the illuminating unit is lower than a reference value, the illuminating unit is replaced or an amplification degree of a brightness signal is adjusted.

The inspection wafer is transferred from a dedicated carrier, which has been transferred to a loading port of the coating and developing system, to the inspection apparatus by means of a transfer mechanism of the coating and developing system. Transporting of the dedicated carrier to the loading port needs labor and time. Further, since transferring of product wafers by the transfer mechanism must be stopped while the inspection wafer is being transferred between the dedicated carrier and the inspection apparatus, the product wafers cannot be processed in the coating and developing system during the aforementioned operations for maintenance of the inspection apparatus. Thus, the maintenance work may decrease the throughput of the coating and developing system. On the other hand, if the frequency of the time-consuming, inconvenient maintenance work is lowered, a usable illuminating unit may be replaced uneconomically, or the inspection of the product wafers may be performed under the condition that the illuminance of the illuminating unit is lower than the reference value, resulting in low precision of the inspection.

JP2001-201431A (corresponding to U.S. Pat. No. 6,456,373 B1) describes an illuminating unit in which the intensity and the spectral distribution of a light emitted from a lamp are compared with references, and whether replacement of the lamp is required or not is alarmed based on the result. However, JP2001-201431A does not describe the above problem in connection with the inspection which is conducted with reference to the displayed image.

SUMMARY OF THE INVENTION

In an embodiment disclosed herein, there is provided a technique for preventing occurrence of trouble in inspection of a substrate, which is caused by a lowered illuminance of an illuminating unit, without transferring a substrate for adjustment to an apparatus.

In one embodiment, there is provided a substrate processing apparatus, which includes: a casing; a table disposed in the casing for placement of a substrate thereon; an illuminating unit provided to illuminate the substrate, placed on the table, with a light; an imaging unit having an imaging device provided to image the substrate placed on the table illuminated with the light; a mode selection unit configured to select one of an inspection mode in which an inspection of a substrate placed on the table is performed based on an image of the substrate obtained by the imaging unit, and a maintenance mode in which inspection of illuminance of the illuminating unit is performed; a light-guiding member disposed in the casing to guide the light emitted from the illuminating unit to the imaging device; a judging unit configured, upon execution of the maintenance mode, to judge whether or not a level of a brightness signal obtained by the imaging device falls within a predetermined allowable range when a light emitted from the illuminating unit falls on the imaging device via the light-guiding member; and an alarming unit configured to alarm, if the judging unit judges that the value of the brightness signal is out of the predetermined allowable range, that replacement of the illuminating unit is required.

In another embodiment, there is provided a substrate inspection apparatus, which includes: a casing; a table disposed in the casing for placement of a substrate thereon; an illuminating unit provided to illuminate the substrate, placed on the table, with a light; an imaging unit having an imaging device provided to image the substrate placed on the table illuminated with the light; a mode selection unit configured to select one of an inspection mode in which an inspection of a substrate placed on the table is performed based on an image of the substrate obtained by the imaging unit, and a maintenance mode in which inspection of illuminance of the illuminating unit is performed; a light-guiding member disposed in the casing to guide the light emitted from the illuminating unit to the imaging device; an amplifying unit configured to amplify, at an adjustable amplification degree, a brightness signal outputted from the imaging device; and an amplification degree adjusting unit configured, upon execution of the maintenance mode, to adjust the amplification degree such that a level of the brightness signal outputted from the amplifying unit falls within a predetermined range when a light emitted from the illuminating unit falls on the imaging device via the light-guiding member.

In one modification of the embodiment, the substrate inspection apparatus may further include: a judging unit configured to judge whether or not the amplification degree adjusted by the amplification degree adjusting unit exceeds a predetermined allowable limit; and an alarming unit configured to alarm, if the judging unit judges that the amplification degree adjusted by the amplification degree adjusting unit exceeds the predetermined allowable limit, that replacement of the illuminating unit is required. In another modification of the embodiment, the substrate inspection apparatus may further include: a data storage unit configured to store values of the amplification degree adjusted by the amplification degree adjusting unit, and time periods from a time point when the illuminating unit is replaced to respective time points when the values of the amplification degree are adjusted; and a display unit configured to display the values of the amplification degree and the time periods, with the values of the amplification degree and the time periods being correlated with each other.

In yet another modification of the embodiment, the light-guiding member is provided in such a manner that the light emitted from the illuminating unit reaches the imaging device in the maintenance mode, while the light emitted from the illuminating unit does not reach the imaging device in the inspection mode. In this case, the light-guiding member may be provided in such a manner that a light path, along which the light emitted from the illuminating unit travels from the light-guiding member to the imaging device when the maintenance mode is performed, is interrupted by a substrate placed on the table when the inspection mode is performed. Alternatively, the substrate inspection apparatus further includes a drive mechanism configured to move the light-guiding member relative to the illuminating unit between a first position at which the light emitted from the illuminating unit is guided to the imaging device and a second position at which the light emitted from the illuminating unit is not guided to the imaging device. In yet another modification of the embodiment, the light-guiding member comprises a reflector provided to reflect the light emitted from the illuminating unit.

In yet another embodiment, there is provided a method of operating a substrate inspection apparatus, wherein the substrate inspection apparatus include a casing, a table disposed in the casing for placement of a substrate thereon, an illuminating unit provided to illuminate the substrate, placed on the table, with a light, and an imaging unit having an imaging device provided to image the substrate placed on the table illuminated with the light, and wherein the substrate inspection apparatus is configured to allow inspection of a substrate based on an image, obtained by the imaging unit, of the substrate illuminated with the light of the illuminating unit. The method may include: guiding a light emitted from the illuminating unit to the imaging device via a light-guiding member disposed in the casing; judging whether or not a level of a brightness signal obtained by the imaging device falls within a predetermined allowable range when a light emitted from the illuminating unit falls on the imaging device via the light-guiding member; and alarming, if it is judged that the value of the brightness signal is out of the predetermined allowable range, that replacement of the illuminating unit is required. Alternatively, the method may include: guiding a light emitted from the illuminating unit to the imaging device via a light-guiding member disposed in the casing; amplifying a brightness signal outputted from the imaging device at an amplification degree; and adjusting the amplification degree such that a level of the amplified brightness signal falls within a predetermined range.

In one modification of the embodiment, the method may further include: placing the light-guiding member in condition that the light-guiding member does not guide the light emitted from the illuminating unit to the imaging device, when a substrate is illuminated with the light emitted from the illuminating unit to be imaged by the imaging unit.

In yet another embodiment, there is provided a computer readable, non-transitory storage medium for performing the aforementioned methods.

DETAILED DESCRIPTION OF THE INVENTION

Figure 1:
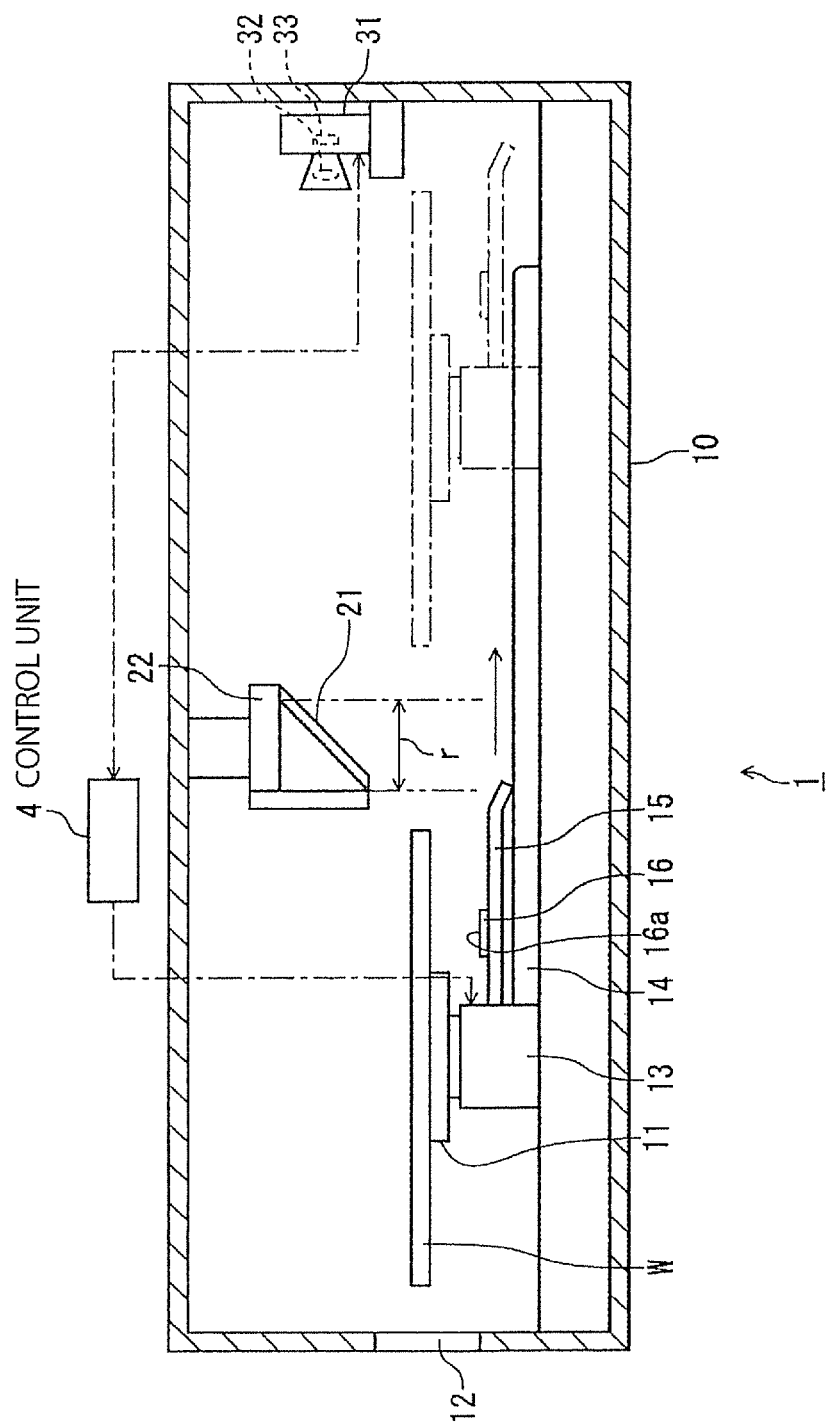
FIG. 1 is a vertically-sectioned, longitudinal cross sectional view of a substrate inspection apparatus.
Figure 2:
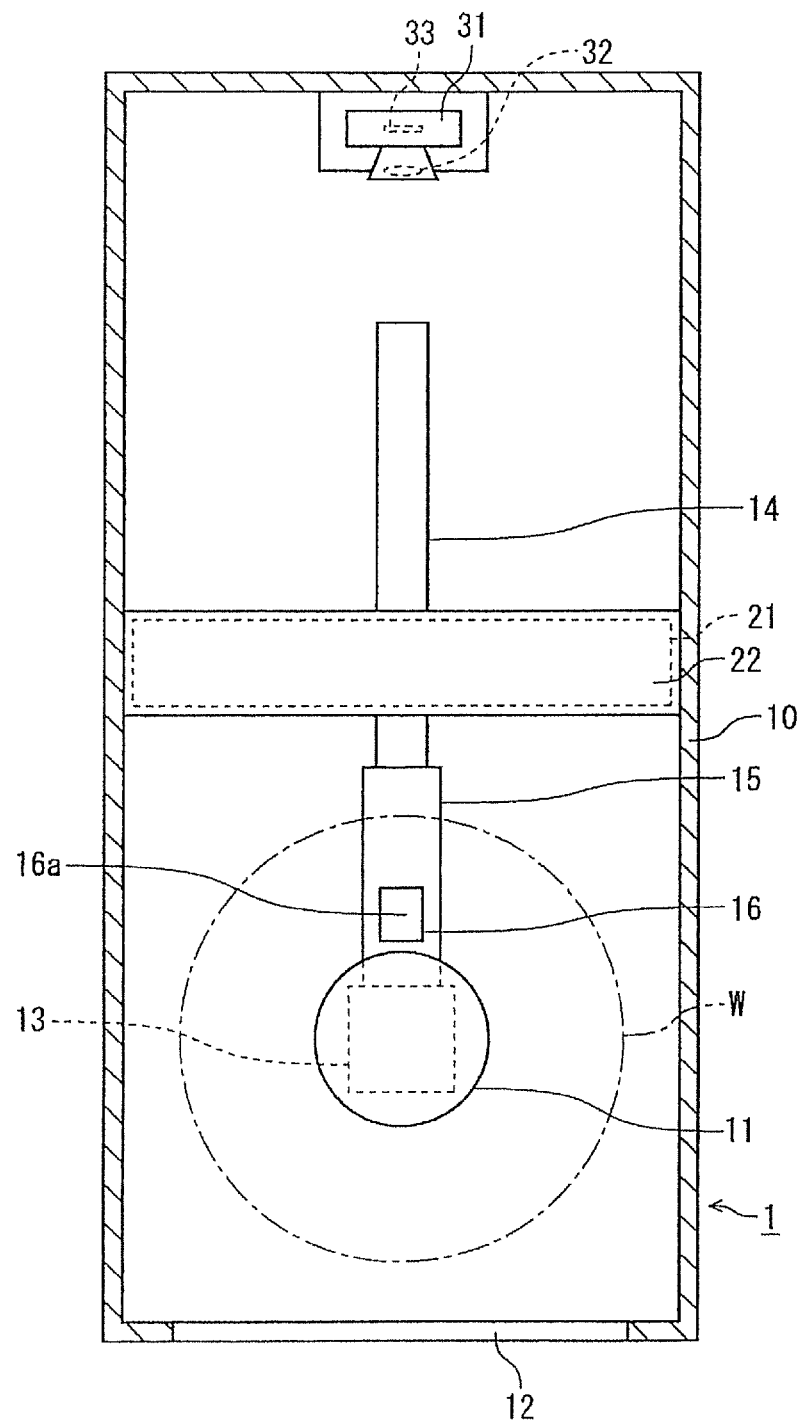
FIG. 2 is a horizontal cross sectional view of the substrate inspection apparatus.

An embodiment of a substrate inspection apparatus 1 is described. FIG. 1 is a vertically-sectioned, longitudinal cross sectional view of a substrate inspection apparatus, and FIG. 2 is a longitudinal cross sectional view of the substrate inspection apparatus. The substrate inspection apparatus 1 includes a table 11 disposed in a casing 10. The table 11 is configured to hold, by suction, a central portion of the back surface of a wafer W so as to horizontally hold the wafer W. In the drawings, the reference numeral 12 depicts a load port through which the wafer W is loaded into and unloaded from the casing 10. The wafer W has been subjected to photolithographic processes, and thus a resist film having a predetermined pattern is formed on the front surface of the wafer W.

The table 11 is supported by a horizontal drive unit 13. Herebelow, for convenience of the explanation, the left side of the substrate inspection apparatus 1 in FIG. 1 where the load port 12 is provided is referred to as "front side", while the right side in FIG. 1 is referred to as "rear side"; and the left side of the substrate inspection apparatus 1 in FIG. 2 is referred to as "left side", while the right side in FIG. 1 is referred to as "right side". A guide rail 14 is laid on a floor surface of the substrate inspection apparatus 1 to extend from the front side toward the rear side. The horizontal drive unit 13 is horizontally movable along the guide rail 14. A cover 15 extends from the horizontal drive unit 13 toward the rear side of the casing 10 to cover an upper surface of the guide rail 14. The task of the cover 15 is to prevent a light reflected from the guide rail 14 from traveling toward an imaging camera 31, when the imaging camera 31 is picking up the image of the wafer W. A reflector plate 16 is disposed on an upper surface of the cover 15. The reflector plate 16 is moved, together with the table 11, between the front side and the rear side in the casing 10, in accordance with the movement of the horizontal drive unit 13. The reference numeral 16a depicts a reflection plane of the reflector plate 16. The reflector plate 16 will be further described later.

An elongated half mirror 21 extending in a right and left direction of the casing 10 is disposed above the guide rail 14. The half mirror 21 is slanted with respect to a horizontal plane. An illuminating unit 22 is disposed above the half mirror 21 to emit a light downward through the half mirror 21. The illuminating unit 22 may comprise light emitting diodes (LEDs), for example, and is replaceable.

Figure 3:
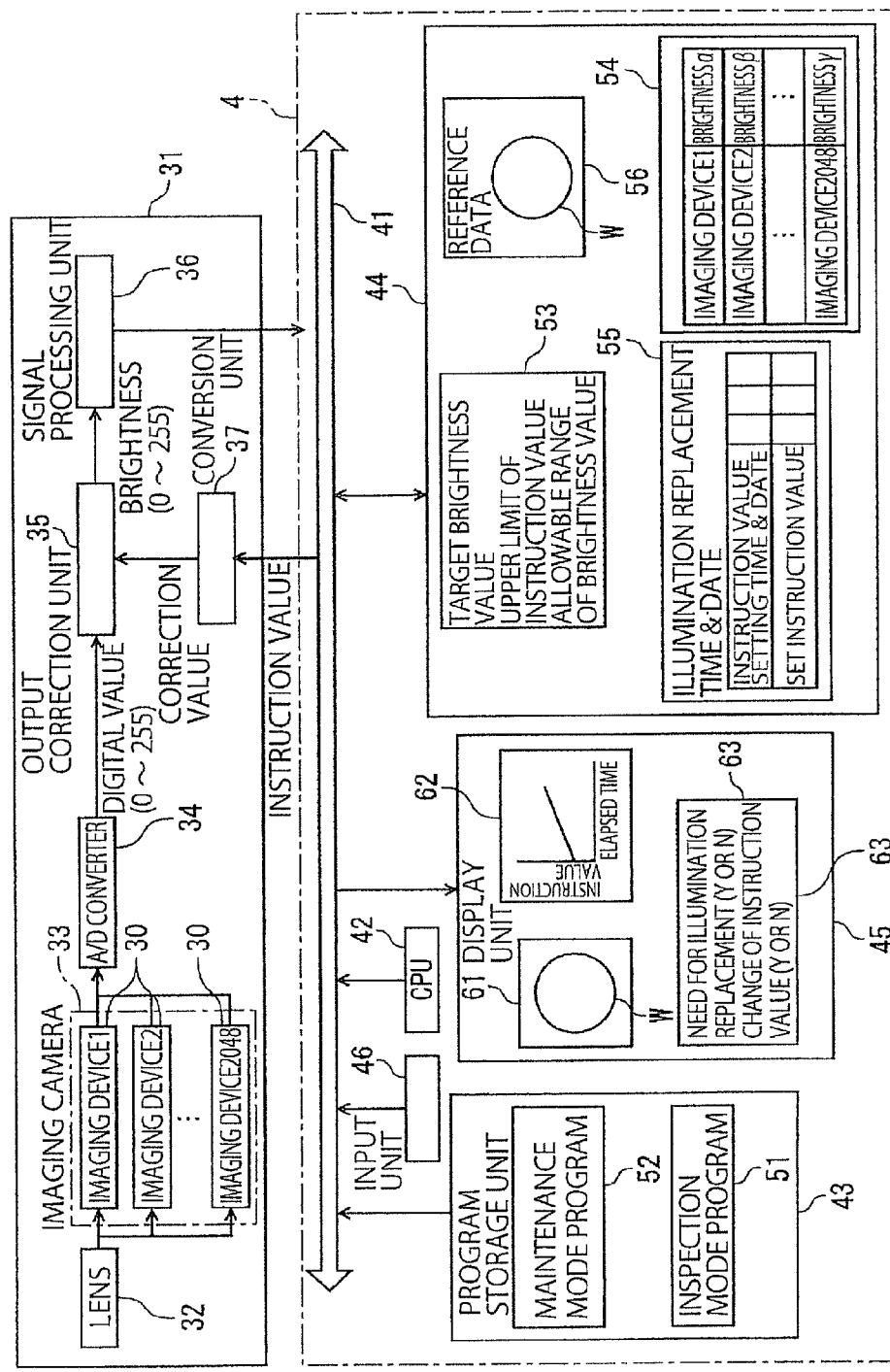
FIG. 3 is a block diagram of a control unit and an imaging camera of the substrate inspection apparatus.

An imaging camera 31 is disposed on the rear side of the half mirror 21. The imaging camera 31 includes a lens 32 and an imaging device array 33 on which the lens 32 produces a focused image. The imaging device array 33 is composed of imaging devices 30 comprising a plurality of (e.g., 2048) CCD devices (pixels) arranged laterally in a row. The imaging camera 31 is provided in such a manner that the imaging camera 31 can pick up the image of the whole wafer W while the wafer W is being moved. The imaging camera 31 will be further described with reference also to the block diagram of FIG. 3. In FIG. 3, in order to facilitate understanding, the imaging devices 30 are numbered from 1 to 2048. The imaging devices 30 are connected to an A/D (analogue/digital) converter 34. An output correction unit 35 comprising an amplification unit is subsequently connected to the A/D converter 34. A signal processing unit 36 is subsequently connected to the output correction unit 35. A light incident on the imaging device array 33 is opto-electrically converted by the imaging device array 33 into analogue signals. The analogue signals are outputted from each of the imaging devices 33 in a predetermined order to the A/D converter 34. The analogue signals are converted into digital signals of 256 levels (numerical values 0 to 255) by the A/D converter 34, and the digital signals are outputted to the output correction unit 35.

The levels of the digital signals (numerical values 0 to 255) indicate the quantity of light incident on respective imaging devices 30, i.e., the brightness of an imaged object. The brightness herein means an intensity of light reflected from a secondary light source, i.e., the wafer W and the reflector plate 16, toward the imaging camera 31. The brightness is a value, having no unit of quantity, represented by a gray level of an image. The output correction unit 35 multiplies the numerical values, each expressing the brightness obtained by respective imaging devices 30, by a predetermined correction value (i.e., a gain or an amplification factor), so as to corrected output digital signals also of 256 levels (numerical values from 0 to 255). Namely, the output correction unit 35 has a function for adjusting a sensitivity of the imaging camera 31 by correcting the brightness signals outputted from the respective imaging devices 30 with the same correction value. Thus, the corrected image has a higher brightness with increasing of the correction value.

The signal processing unit 36 performs a shading correction and a "γ (gamma)" correction, in this order, to the signals outputted from the output correction unit 35. In the shading correction, the brightness values from the imaging devices 30 are independently amplified at respective amplification degrees that are respectively predetermined for the imaging devices 30. Then, in the γ correction, the brightness values of the images from the respective imaging devices 30 are corrected such that the brightness values of the image from the respective imaging devices 30 are uniformly increased according to a predetermined function, so that the corrected signals are outputted as digital signals corresponding to also of 256 levels (numerical values from 0 to 255).

Figure 4:
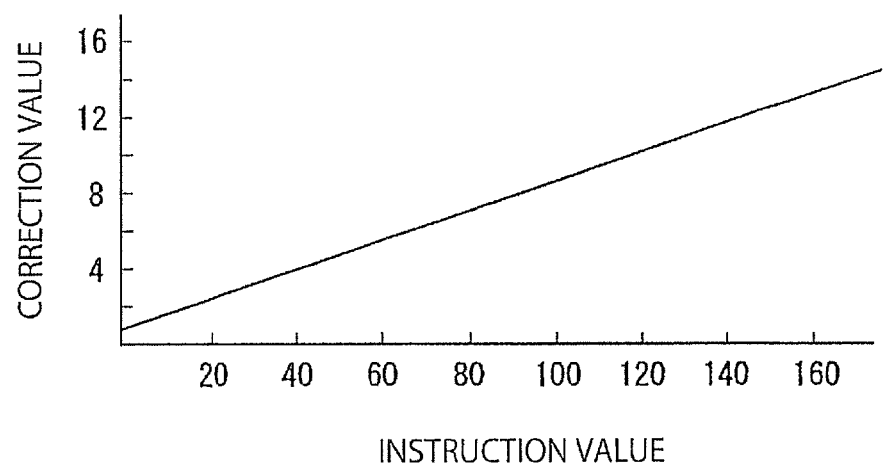
FIG. 4 is a graph showing an example of a correlation between an instruction value and a correction value.

The imaging camera 31 is provided with a conversion unit 37 which outputs a correction value used for the above-described correction by the output correction unit 35. In order to correct the brightness of an image, an instruction value is transmitted from a control unit 4, which will be described below, to the conversion unit 37. The conversion unit 37 has a storage unit storing a corresponding relationship between the instruction value and the correction value, an example of which is shown in FIG. 4. Based on the instruction value and the corresponding relationship, the conversion unit 37 determines a correction value, and outputs the correction value to the output correction unit 35. The reason for converting the instruction value to the correction value is to compensate variation due to individual difference between imaging cameras 31. That is, the corresponding relationship is set to each imaging camera 31 individually. Since a digital value outputted from the A/D converter 34 is relatively low in general, the corresponding relationship is set such that a correction value of 1 (one) or more may be outputted (see FIG. 4).

Figure 5:
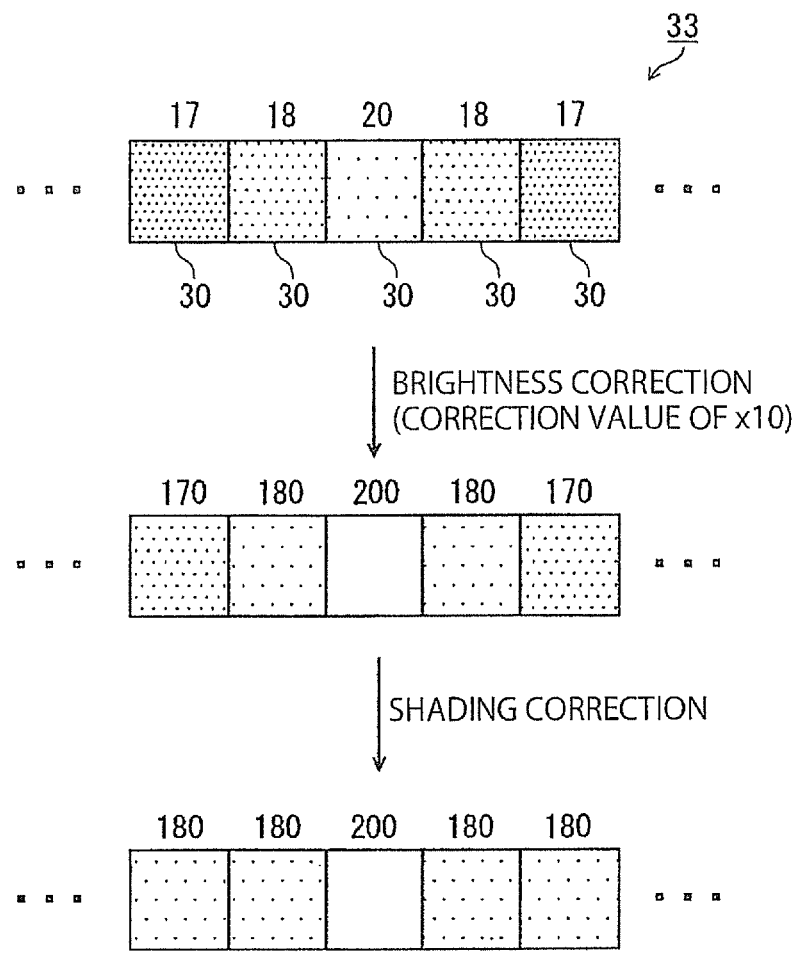
FIG. 5 is an explanatory diagram showing steps for correcting an image.

FIG. 5 is a diagram schematically showing how the brightness signals and thus the image is corrected. The upper part of FIG. 5 shows the imaging devices 30 (i.e., pixels) of the imaging device array 33 on which the reflected light from the object (e.g., wafer) falls. The density of the dots corresponds to the darkness. The brightness values of the brightness signals after A/D conversion are shown above the respective imaging devices 30. The middle part of FIG. 5 shows the brightness values of the brightness signals after correction by the output correction unit 35. In this example, the correction value is 10 (ten), and the brightness values of the brightness signals are thus amplified tenfold. The lower part of FIG. 5 shows the brightness values of the brightness signals after the shading correction. Thereafter, the γ correction is performed, and the brightness signals after the corrections (i.e., the corrected image) are stored in the control unit 4.

Returning to FIG. 1, the light from the illuminating unit 22 passes through the half mirror 21 and falls on an illuminated area, which is shown by the character "r", below the half mirror 21. A reflection light from the object in the illuminated area "r" is reflected on the half mirror 21 so as to be taken into the imaging camera 31. Namely, the imaging camera 31 can pick up the image of the object located in the illuminated area "r". While the wafer W is moved along the guide rail 14 below the half mirror 21 from the front side toward the rear side, the imaging camera 31 intermittently images the wafer W in accordance with a control signal of the control unit 4, so that the overall surface of the wafer W is imaged.

The substrate inspection apparatus 1 performs, upon automatic or manual selection, one of two operation modes, one being an inspection mode in which the wafer W is imaged as described above so as to inspect the surface thereof, and the other being a maintenance mode in which the brightness of the image, which is obtained by the imaging camera 31 without any wafer W being loaded in the substrate inspection apparatus 1, is adjusted, and whether or not the illuminating unit 22 is required to be replaced is inspected. To be specific, in the maintenance mode, depending on the values of the brightness signals of the image obtained by imaging the reflector plate 16, a signal amplification degree (i.e., the correction value and an instruction value corresponding to this correction value) in the output correction unit 35 is set (determined) so as to control the brightness of the image to be a suitable value. If the instruction value exceeds an allowable limit, replacement of the illuminating unit 22 is alarmed to the user, in order to prevent deterioration of the image caused by amplifying noises in the signals.

Figure 6:
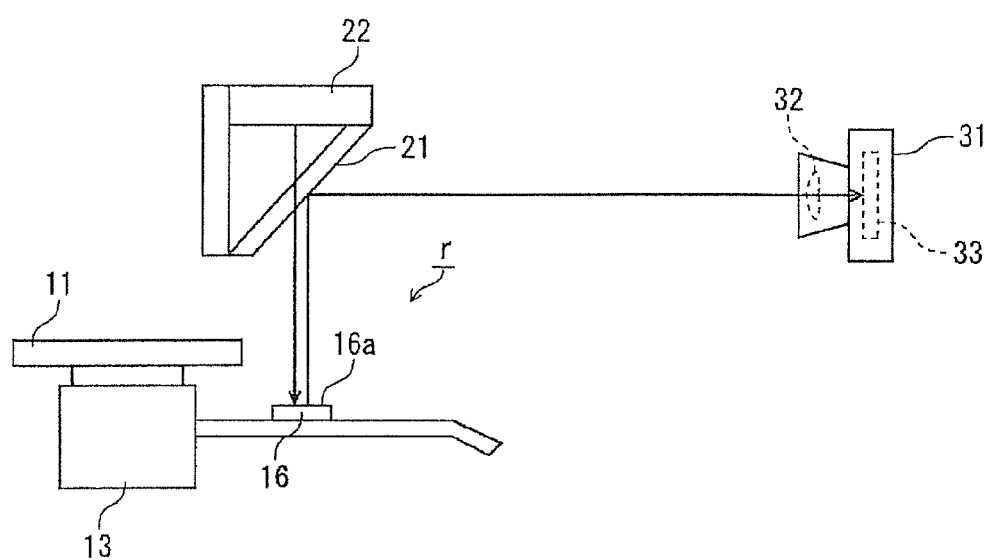
FIG. 6 is an explanatory diagram showing how a light is guided by a reflector plate to the imaging camera.

The reflector plate 16 is described in more detail. The reflector plate 16 is used when the maintenance mode is performed. As shown in FIG. 6, when the reflector plate 16 is positioned in the illuminated area "r", the reflector plate 16 reflects the light emitted from the illuminating unit 22. As shown by the arrow in FIG. 6, the light reflected on the reflector plate 16 is then reflected on the half mirror 21 to fall on the imaging device array 33 of the imaging camera 31. As shown in FIG. 1, when the inspection mode is performed, the reflector plate 16 is located below the wafer W placed on the table 11. Thus, a light path between the reflector plate 16 and the imaging device array 33, which is shown by the arrow in FIG. 6, is interrupted by the wafer W, whereby the reflector plate 16 is not imaged by the imaging camera 31. The reason why reflector plate 16 is located on such a position is to avoid a situation where, during the inspection of the wafer W, the light travelling from the reflector plate 16 falls on the imaging device array 33 of the imaging camera 31 to invite light saturation (i.e., electric charges generated in the imaging device array 33 are saturated) which results in blurring of an obtained image of the wafer W.

Next, the control unit 4 comprising a computer is described with reference to FIG. 3. The control unit 4 includes a bus 41, connected to which are a CPU 42 for performing various calculations, a program storage unit 43, a memory 44, a display unit 45 and an input unit 46. The program storage unit 43 stores a program 51 for performing the inspection mode (inspection mode program 51) and a program 52 for performing the maintenance mode (maintenance mode program 52). The programs 51 and 52 are each configured such that, upon execution, control signals are transmitted from the control unit 4 to the respective units of the substrate inspection apparatus 1, so as to carry out the steps of the respective modes as described below. The program storage unit 43 comprises a computer-readable, non-transitory storage medium such as a flexible disc, a compact disc, a hard disc or an MO (magnetoptical disc).

The memory 44 includes: a correction value setting data storage area 53 that stores various data used for setting a correction value used in the output correction unit 35; an image data storage area 54 that stores values of the brightness signals of an image obtained by the imaging camera 31; an instruction value storage area 55 that stores set (determined) instruction values; and a reference data storage area 56 that stores a reference data for judging whether or not a wafer W is acceptable in the inspection mode.

The respective areas of the memory 44 are described in more detail. The correction value setting data storage area 53 stores: a target value of brightness values (Note: actual brightness values of the image of the reflector plate 16 are stored in the image data storage area 54 when the reflector plate 16 is imaged when the maintenance mode is executed); an allowable range of the actual brightness value (or an allowable range of deviation of the actual brightness values from the target value; and an upper limit value of the instruction value. The allowable range ranges from a value slightly or somewhat lower than the target value, to the target value.

When analogue signals are sequentially outputted from the respective imaging devices 30 constituting the imaging device array 33 to the image data storage area 54, the values of the brightness signals of images outputted from the respective imaging devices 30 (converted into digital values) are stored in the image data storage area 54 in predetermined addresses, respectively. The instruction value storage area 55 stores an instruction value determined in the maintenance mode, and the time & date at which the instruction value was determined, with the instruction value and the time & date being correlated. For each time when the instruction value is changed, the instruction value and the time & date are stored again. In addition, the instruction value storage area 55 stores the time & date at which the illuminating unit 22 is replaced. The time & date of the illumination replacement is stored upon operation of the user using the input unit 46. The reference data storage area 56 stores an image of a wafer free of defect (reference wafer). Based on comparison between brightness values of the image of the reference wafer and brightness values of an image of the wafer W stored in the image data storage area 54 in the inspection mode, whether the wafer W has a defect or not is judged.

Next, the display unit 45 which also serves as an alarming unit is described. The display unit 45 includes a wafer displaying area 61, an instruction value displaying area 62, and an alarm displaying area 63. The wafer displaying area 61 is an area where image data stored in the image data storage area 54 are displayed. Namely, when the inspection mode is performed, an image of a wafer W obtained by the imaging camera 31 is displayed on the wafer displaying area 61. The instruction value displaying area 62 displays variation of the instruction value with time from the time point when the illuminating unit 22 was replaced most recently, based on data stored in the instruction value storage area 55 of the memory 44.

Figure 7:
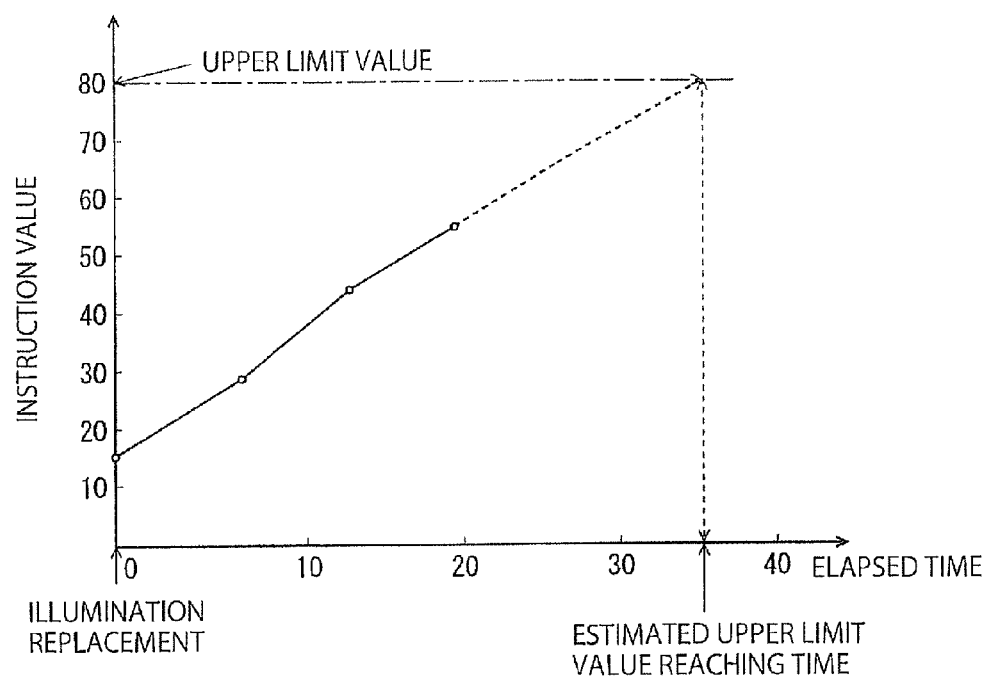
FIG. 7 is a graph showing the change of the instruction value with the elapsed time (operating time) from the replacement of the illuminating unit.

FIG. 7 shows an example of a graph displayed in the instruction value displaying area 62. The axis of abscissa of the graph shows an elapsed time (unit: hour) from the time point when the illuminating unit 22 was replaced, where the elapsed time is determined based on the difference between the illuminating unit replacement time & date and the set time & date of the instruction value, which are stored in the instruction value storage area 55. The axis of ordinate of the graph shows the determined (set) instruction value. The instruction values stored in the instruction value storage area 55 are plotted on the graph in correlation with their set time & date. The graph also shows the upper limit value of the instruction value stored in the correction value setting data storage area 53.

The "estimated upper limit value reaching time" in the graph means the time at which the instruction value is estimated to reach the upper limit. The "estimated upper limit value reaching time" is calculated assuming that the increasing rate of the instruction value after the instruction value "α" has been set is $(α-β)/(t1-t2)$ after the instruction value "α" has been set, where "α" is the instruction value which was set most recently, "β" the instruction value which was set immediately before the time when the instruction value "α" was set, "t1" is the time when the instruction value "α" was set, and "t2" is the time when the instruction value "β" was set. The display of the instruction value displaying area 62 is not limited to that shown in FIG. 7. The instruction value displaying area 62 may display a table in which periods from the time point when the illuminating unit is replaced to the time points when respective instruction values are set, and the respective set instruction values are correlated to each other. The correction value may be displayed instead of the instruction value.

The alarm displaying area 63 is an area for displaying whether or not replacement of the illuminating unit 22 is required, which requirement is determined based on the set instruction value, so as to alarm the user. The alarm displaying area 63 also displays whether or not the instruction value was (at this time) changed. The alarming method for alarming the user that the illuminating unit should be replaced and that the instruction value was changed is not limited to the displaying on the screen. An alarm sound may be used.

The input unit 46 is composed of, e.g., a plurality of buttons and the like. As described above, when the illuminating unit 22 is replaced, the user can input, by the input unit 46, into the control unit 4 data indicating that the illuminating unit 22 is replaced. Also, the user can switch the operation mode between the maintenance mode and the inspection mode, by using the input unit 45.

Next, the procedure performed in the maintenance mode and the inspection mode will be described below.

<Maintenance Mode>

Figure 8:
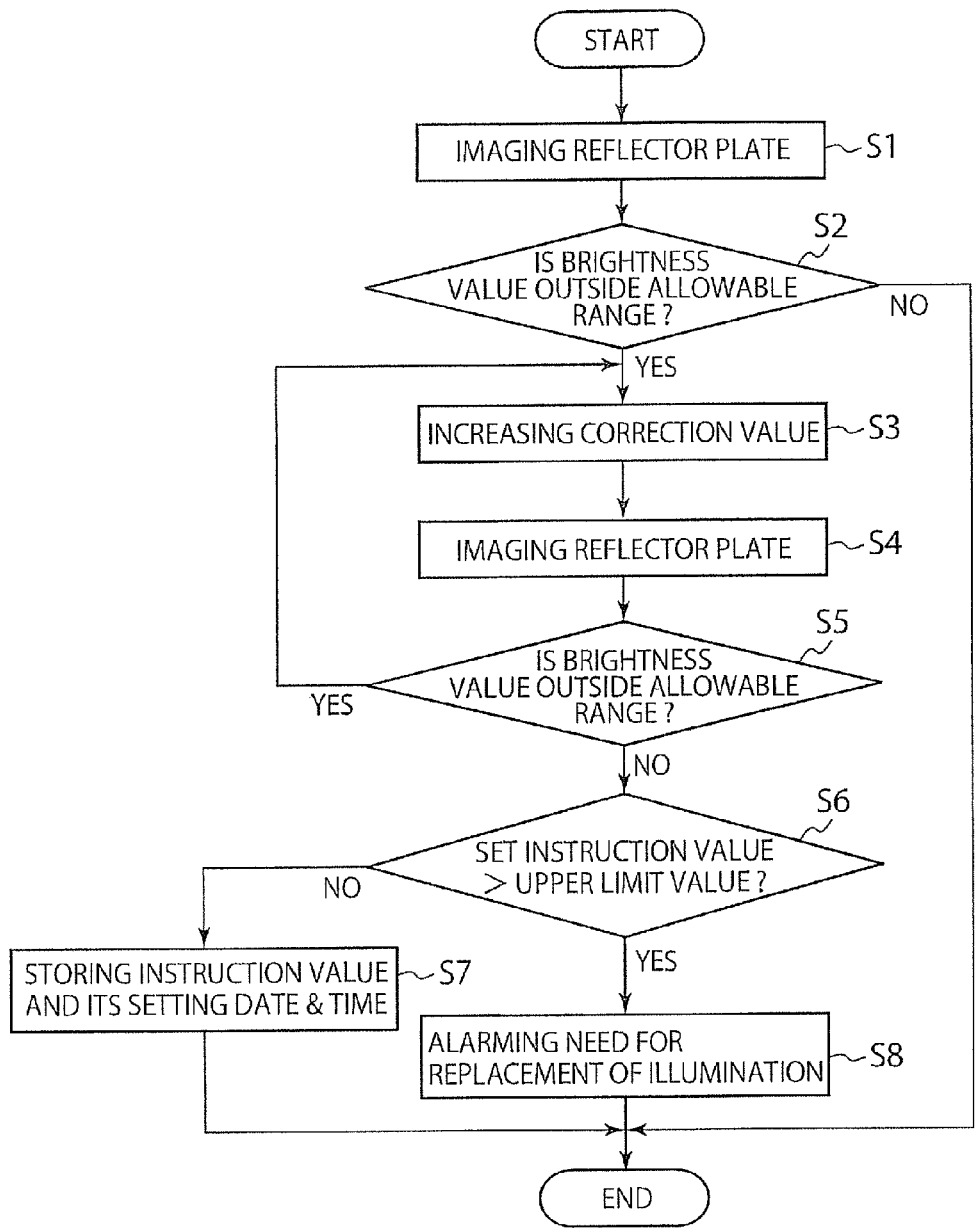
FIG. 8 is a flowchart of a maintenance mode.

The maintenance mode will be described with reference to a flowchart of FIG. 8. When the user performs a predetermined operation using the input unit 46, the table 11 is moved forward by the horizontal drive unit 13 from a receiving position at which the table 11 receives the wafer W, which is located on the front side in the casing 10. In accordance with the movement of the horizontal drive unit 13, the reflector plate 16 is moved forward so as to be positioned in the illuminated area "r" of the illuminating unit 22 as shown in FIG. 6. Thus, a light emitted from the illuminating unit 22 is reflected on the reflector plate 16, so that the light is guided toward the imaging camera 31 via the half mirror 21. Then, a not-shown shutter of the imaging camera 31 is opened, so that the light from the reflector plate 16 falls on the lens 32 whereby an image is formed on the imaging device array 33 (step S1).

As described above, analog signals are generated by the respective imaging devices (pixels) 30 of the imaging device array 33 and are outputted at respective output levels corresponding to quantities of light received by the respective imaging devices 30, and the analogue signals are converted to digital signals by the A/D converter 34. The control unit 4 outputs, to the imaging camera 31, an instruction value (this value is hereinafter referred to as "a" for convenience of explanation), which has been most recently stored in the instruction value storage area 55. The conversion unit 37 outputs a correction value corresponding to the instruction value "a". Then, the digital values from the A/D converter 34 are multiplied by the correction value in the output correction unit 35, whereby digital values of brightness in the range of 0 to 255 are outputted. Then, as described above, the brightness values are further corrected by the signal processing unit 36. The corrected brightness values are stored in the addresses, respectively corresponding to the imaging devices 30, of the image data storage area 54 of the memory 44.

Following thereto, from all the brightness signal values, brightness signal values associated with the imaging devices 30 onto which the light from the reflector plate 16 are extracted and the average of the extracted brightness value is calculated. Then, it is judged whether or not the average of the brightness average falls within the allowable range stored in the correction value setting data storage area 53 (step S2). The imaging devices 30, the brightness signal values from which are used for average calculation, are previously determined.

In the step S2, if the average brightness value is judged to fall within the allowable range, the alarm displaying area 63 of the display unit 45 displays a sign informing that replacement of the illuminating unit is not required and a sign informing that the instruction value is not changed. On the other hand, if the average brightness value is judged to be smaller than the target value and out of the allowable range, the instruction value "a" is increased by one ("a+1") (step S3), and the reflector plate 16 is again imaged in the same way as that in step S1 (step S4). Then, the output correction unit 35 amplifies the brightness signals using a correction value corresponding to the instruction value "a+1", and the brightness signal values from the respective imaging devices 30 are stored in the image data storage area 54. Thereafter, in the same way as that in step S2, an average brightness value is calculated, and whether or not the average value falls within the allowable range is judged (step S5).

In step S5, when the average brightness value is judged to be smaller than the target value and out of the allowable range, the instruction value further increased by one ("a+2"). Then, the reflector plate 16 is again imaged, and whether the average brightness value falls within the allowable range is judged. If the average brightness value is smaller than the target value and out of the allowable range, the instruction value is further increased by one ("a+3"). Then, the reflector plate 16 is again imaged, and whether the average brightness value fall within the allowable range is judged. As mentioned above, steps S3 to S5 are repeatedly performed while increasing the instruction value one by one in step 3, as long as the average brightness value is judged to be smaller than the target value and out of the allowable range in step 5.

In step S5, if the average brightness average value is judged to be larger than the target value and out of the allowable range, it is judged whether or not a newly set instruction value is larger than the upper limit value of the instruction value stored in the correction value setting data storage area 53 (step S6). In step S6, if the set instruction value is judged to be not larger than the upper limit value, the time & date at which the judgment is made and the set instruction value are stored in a correlated manner in the instruction value storage area 55 (step S7). Simultaneously, the alarm displaying area 63 displays a sign informing that the instruction value is changed. Further, the graph shown in the instruction value displaying area 62 is updated, in other words, a new point corresponding to the newly stored instruction value and the set time & date is plotted on the graph and the line on the graph is extended. In addition, the "estimated upper limit value reaching time" is calculated, and the indication thereof on the graph is updated.

If the newly-set instruction value is judged to be larger than the upper limit value, an alarm informing that replacement of the illuminating unit is required is outputted to the alarm displaying area 63 (step S8). The aforementioned flow is performed upon execution of the maintenance mode program 52, which realizes a judging unit and an amplification degree adjusting unit. When such an alarm is outputted, the user enters the substrate inspection apparatus 1 and replaces the illuminating unit 22. After the replacement of the illuminating unit 22, the user inputs data indicating execution of the replacement, using the input unit 46. Thus, the data stored in the instruction value storage area 55 is reset, so that the graph of the instruction value display area 62 of the display unit 45 is reset. In addition, the time & date when the user inputs data indicating execution of the replacement is newly stored, as the replacement time & date of the illuminating unit 22. After the illuminating unit 22 has been replaced, when the maintenance <Inspection Mode>

After the maintenance mode has been finished, the inspection mode is started upon user's predetermined operation through the input unit 46. A wafer W is loaded into the substrate inspection apparatus 1 by a not-shown transfer mechanism, and the central portion of the back surface of the wafer W is held by the table 11, which is located on the receiving position shown by solid lines in FIG. 1. Thereafter, the table 11 holding thereon the wafer W is moved forward (toward the imaging camera 31) in the casing 10. When the table 11 is located in the illuminated area "r" below the illuminating unit 22, the image of the wafer W is picked up by the imaging camera 31. As described above, the whole surface of the wafer W is imaged by intermittently imaging the wafer W that is continuously moved forward.

At this time, the most-recently set instruction value is outputted from the control unit 4 to the imaging camera 31. An output from the A/D converter 34 is corrected by a correction value corresponding to the instruction value, and the brightness signals of the image are amplified. Then, similarly to the maintenance mode, after the values of the brightness signals of the image has been corrected, the brightness values are stored in the image data storage area 54 of the memory 44. Based on the brightness values, the image of the wafer W (a visualized picture image of the wafer) is displayed on the wafer displaying area 61 of the display unit 45, and this image is compared to the image of the reference wafer (e.g., through visual inspection or through automatic image analysis) so as to judge whether or not the imaged wafer W has defects (particles, scratches, unacceptable line-width deviation, or the like). The aforementioned series of processes are performed upon execution of the inspection mode program 51.

In the foregoing embodiment of the substrate inspection apparatus 1, the reflector plate 16 illuminated with the light emitted by the illuminating unit 22 is imaged by the imaging camera 31, and whether or not replacement of the illuminating unit is required is judged based on the brightness value of the image. Thus, it is not necessary to transport a tool (e.g., inspection wafer) for inspecting an illuminance of the illuminating unit 22 into the substrate inspection apparatus 1, and thus the reduction of throughput of the substrate processing system is avoided. In addition, since the deterioration of the illuminating unit 31 can be compensated by increasing the correction value of the imaging camera 31, the frequency of replacement of the illuminating unit 31 can be reduced, and thus the reduction of throughput of the substrate processing system is avoided.

In addition, in the substrate inspection apparatus, the display unit 45 displays the time periods from the time point when the illumination unit 22 is replaced to respective time points when the instruction value is changed and the respective instruction values, with the time periods and the instruction values being correlated to each other. Thus, the user can see the decreasing rate of the illuminance of the illuminating unit 22 based on the change of the instruction value with time, so that the user can estimate the timing at which the illuminance of the illuminating unit 22 falls below a reference value. Accordingly, it is possible to avoid a situation where a wafer W is inspected with the wafer being illuminated by the illuminating unit 22 having insufficient illuminance, so that an existing defect cannot be detected. It is also possible to avoid a situation where, although the illuminating unit 22 has a sufficient illuminance, the maintenance mode is unnecessarily performed to reduce the throughput, or the illuminating unit 22 is unnecessarily replaced with a new one.

Further, in the substrate inspection apparatus 1, the reflector plate 16 is disposed in such a manner that a light from the reflector plate 16 is interrupted by a wafer W during execution of the inspection mode. Thus, when the wafer W is inspected, it is possible to avoid a situation where a light reflected from the wafer W and a light reflected from the reflector plate 16 are both supplied to the imaging camera 31, which situation may result in the light saturation of the imaging devices 30, i.e., the saturation of the electric charges generated in the imaging devices 30, under which situation proper image data cannot be obtained. Accordingly, the wafer W can be inspected with high precision.

In practice, the illuminating unit 22 may be configured such that the illuminance of the illuminating unit 22 can be changed at multiple levels depending on the situation (e.g., the type of films formed on the wafer W to be inspected), and the target value and the allowable range of the brightness may be set for each level of the illuminance. In such a case, when the illuminating unit 22 is replaced, the level of the illuminance is set. When the maintenance mode is performed, the target value and the allowable range of the brightness corresponding to the set illuminance are read out, and the aforementioned steps S1 to S8 are carried out.

In the above embodiment, the following process is possible. Namely, instead of converting the instruction value to the correction value and outputting the correction value, the control unit 4 may directly output the correction value, and the digital value outputted from the A/D converter 34 may be multiplied by the correction value for amplification. Furthermore, instead of amplifying a signal in a subsequent stage of the A/D converter 34, an analogue signal outputted from each imaging device 30 may be amplified with the use of the correction value, and then the amplified analogue signal may be converted to a digital signal. Furthermore, the user may monitor the instruction value displayed on the display unit 45, and the user may judge replacement timing of the illuminating unit 22 based on the displayed instruction value.

In the foregoing embodiment, when the correction value is set in the maintenance mode, the instruction value is increased one by one. However, the way how to change the instruction value is not limited thereto, but may be as follows: The necessary increment "c" of the instruction value which is required for achieving a predetermined increment (e.g., 5 (five)) of the brightness values of the image data is previously calculated. During execution of the maintenance mode, if the target brightness value is 200 and the actual brightness value is 180, the difference (200−180) is divided by the predetermined increment 5 (five), and then multiplied by the necessary increment "c" ((200−180)/5×c is calculated). Then, the calculated value is added to the instruction value, and the brightness value is again measured. If the measured brightness value is smaller than 200 (target value), the instruction value is increased one by one until the brightness value reaches the target value (or falls within the allowable range), similarly to the foregoing embodiment. On the other hand, if the measured brightness value is larger than 200 (target value), the instruction value is decreased one by one until the brightness value reaches the target value (or falls within the allowable range). In the above steps S2 and S5, the average of the brightness values of the brightness signals obtained from the plurality of imaging devices 30 is compared to the allowable range. However, in place thereof, the brightness values of the brightness signals obtained from the plurality of imaging devices 30 may be independently compared with the allowable range one by one. In this case, when the number of the imaging devices 30, from each of which a brightness signal of a brightness value out of the allowable range, exceed a predetermined number, step S3 in which the correction value is increased may be performed.

Figure 9:
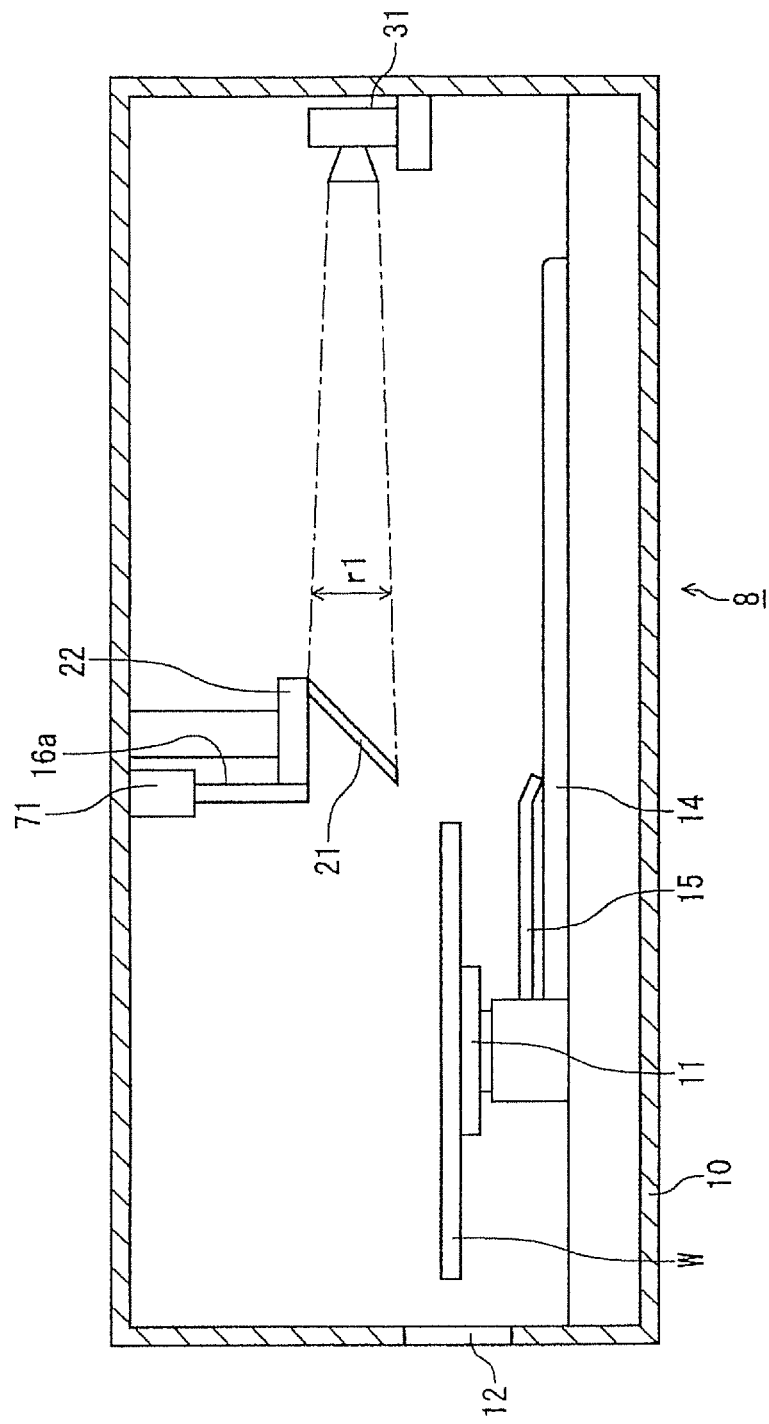
FIG. 9 is a vertically-sectioned, longitudinal cross sectional view of another substrate inspection apparatus.

Next, another embodiment of the substrate inspection apparatus will be described, with reference to FIGS. 9 and 10. The substrate inspection apparatus 8 in this embodiment differs from the substrate inspection apparatus 1 in the previously-described embodiment in that the reflector plate 16 of the substrate inspection apparatus 8 is disposed in a ceiling portion of the casing 10 in front of the half mirror 21 in upright posture. The reflection surface 16a faces the rear side of the casing 10. An elevating mechanism 71 is provided to move the reflector plate 16 vertically. When the inspection mode is performed, the reflector plate 16 is moved to a retracted position outside an imaging area "r1" shown in FIG. 9 which corresponds to the view angle of the imaging camera 31.

Figure 10:
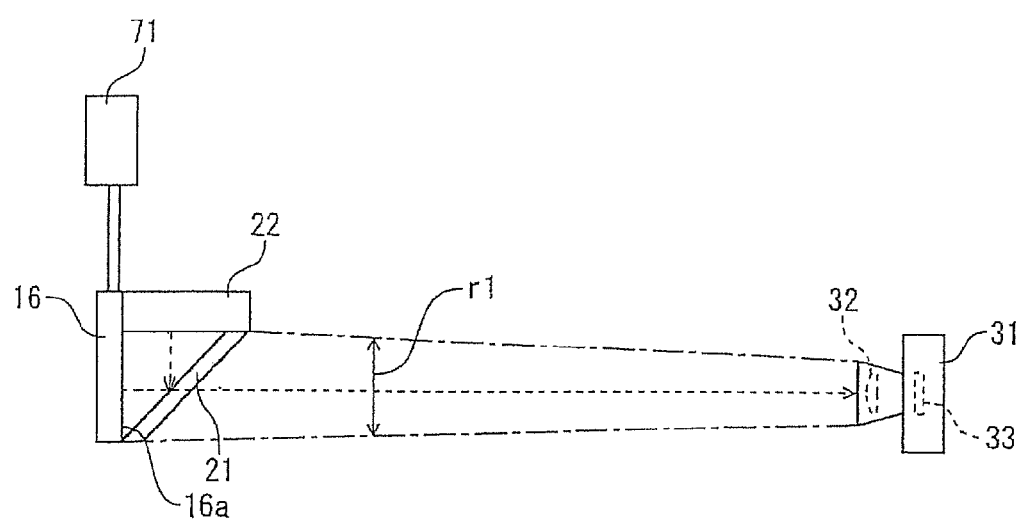
FIG. 10 is a side view of a reflector plate of the substrate inspection apparatus shown in FIG. 9.

When the maintenance mode is performed, as shown in FIG. 10, the reflector plate 16 is lowered by the elevating mechanism 71 to a position inside the imaging area "r1". At this time, as shown by dotted line in FIG. 10, a light emitted from the illuminating unit 22 and reflected on the reflector plate 16 falls on the imaging device array 33 of the imaging camera 31, that is, the reflector plate 16 is imaged. Also with this configuration, similarly to the substrate inspection apparatus 1, it is possible to prevent a situation where excessive amount of light falls on the imaging device array 33 which may result in light saturation.

Figure 11:
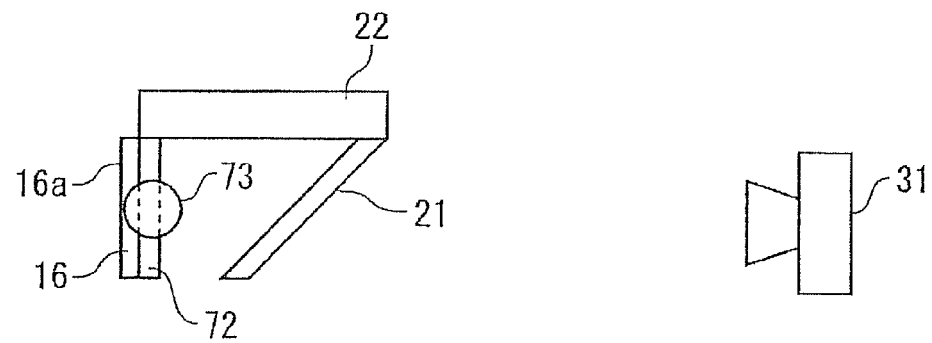
FIGS. 11 to 13 are side views of another reflector plate and related parts showing the operation thereof.
Figure 12:
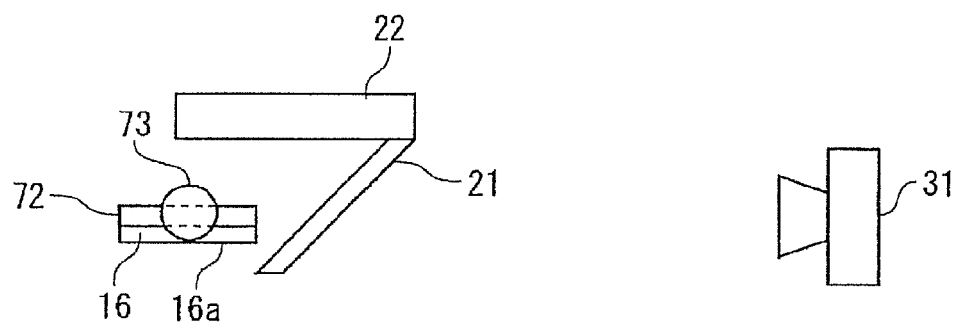
Figure 13:
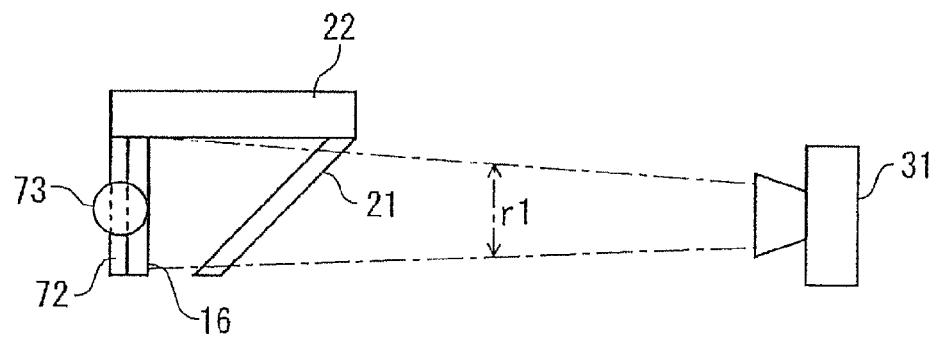

In order to prevent light saturation, the reflector plate 16 may be disposed as shown in FIGS. 11 to 13. In FIG. 11, a support plate 72 is disposed in front of (on the load port side) the half mirror 21. As shown in FIGS. 12 and 13, the support plate 72 can rotate about a horizontal axis by a rotating mechanism 73 disposed on a side wall of the casing 10. The reflector plate 16 is disposed on the support plate 72. When the inspection mode is performed, the reflector plate 16 faces the front side of the casing 10 as shown in FIG. 11. Thus, a light emitted from the illuminating unit 22 does not fall on the reflector plate 16, and the reflector plate 16 is not imaged by the imaging camera 31. When the maintenance mode is performed, the reflection surface 16a faces the rear side of the casing 10. Thus, similarly to the reflector plate 16 of the substrate inspection apparatus 8, the reflector plate 16 can be located in the imaging area "r1" of the imaging camera 31.

Figure 14:
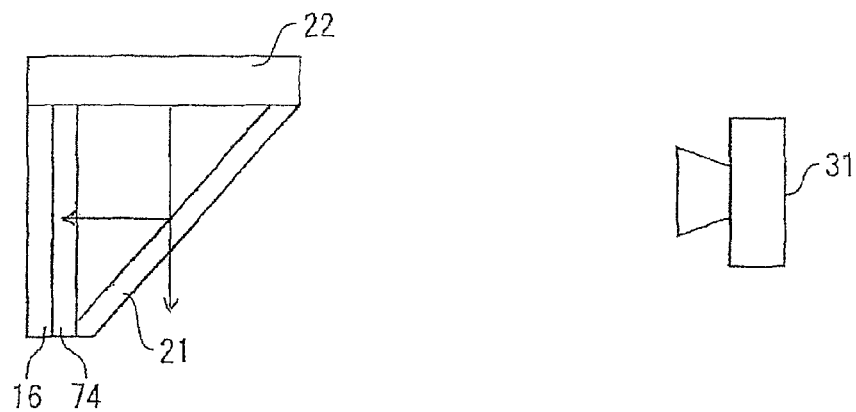
FIGS. 14 and 15 are side views of yet another reflector plate and related parts showing the operation thereof.
Figure 15:
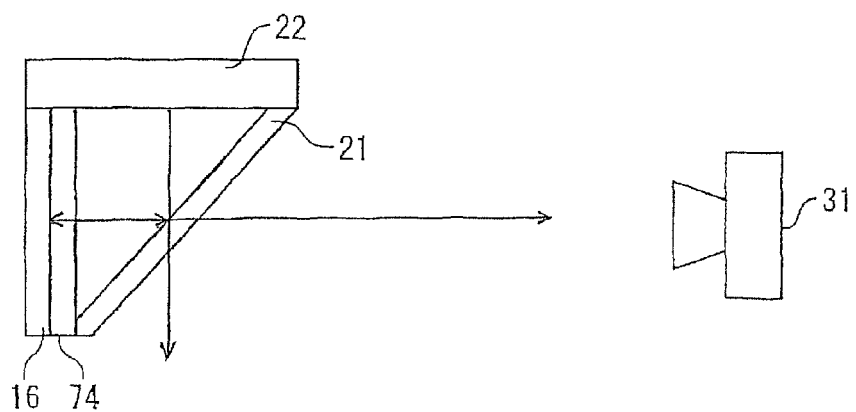

FIG. 14 shows another embodiment of the reflector plate adapted for preventing light saturation. In this embodiment, the reflector plate 16 is disposed in front of the half mirror 21 such that the reflection surface 16a faces the rear side of the casing (i.e., the side of the imaging camera 31). A dimming glass (light control glass) 74 is attached onto the reflection surface 16a of the reflector plate 16. The dimming glass 74 composed of: a liquid crystal sheet, a pair of transparent conductive sheets that sandwich the liquid crystal sheet, and a pair of glass sheets that sandwich the laminate of the liquid crystal sheet and the transparent conductive plates. When no electric voltage is applied to the conductive sheets, a transparency of the dimmer glass 74 is low because liquid crystal molecules are irregularly arranged, whereby a light emitted from the illuminating unit 22 is not reflected by the reflector plate 16. On the other hand, when an electric voltage is applied to the conductive sheets, the transparency of the dimmer glass 74 increases because the liquid crystal molecules are regularly arranged, whereby the light of the illuminating unit 22 transmits through the dimmer glass 74. Therefore, as shown in FIG. 15, the reflector plate 16 reflects the light emitted from the illuminating unit 22, and the reflected light falls on the imaging device array 33 of the imaging camera 31.

In another embodiment (not shown in any drawing), the reflector plate 16 may be disposed on the surface of the table 11, and the table 11 is moved to the illuminated area "r" of the illuminating unit 22 (see FIG. 1) when the maintenance mode is performed.

In a case where the reflector plate 16 is moved by the elevating mechanism 71 or the rotating mechanism 73, and also in a case where the dimming glass 74 is provided, it is preferable that the maintenance mode is performed without any wafer W being located in the casing 10, in order to prevent a light from the reflector plate and a light reflected from a wafer W from falling on the imaging device array 33. However, the maintenance mode may be performed with a wafer W being located on a position outside the illuminated area "r" of the illuminating unit 22 (see FIG. 1) in the casing 10.

Figure 16:
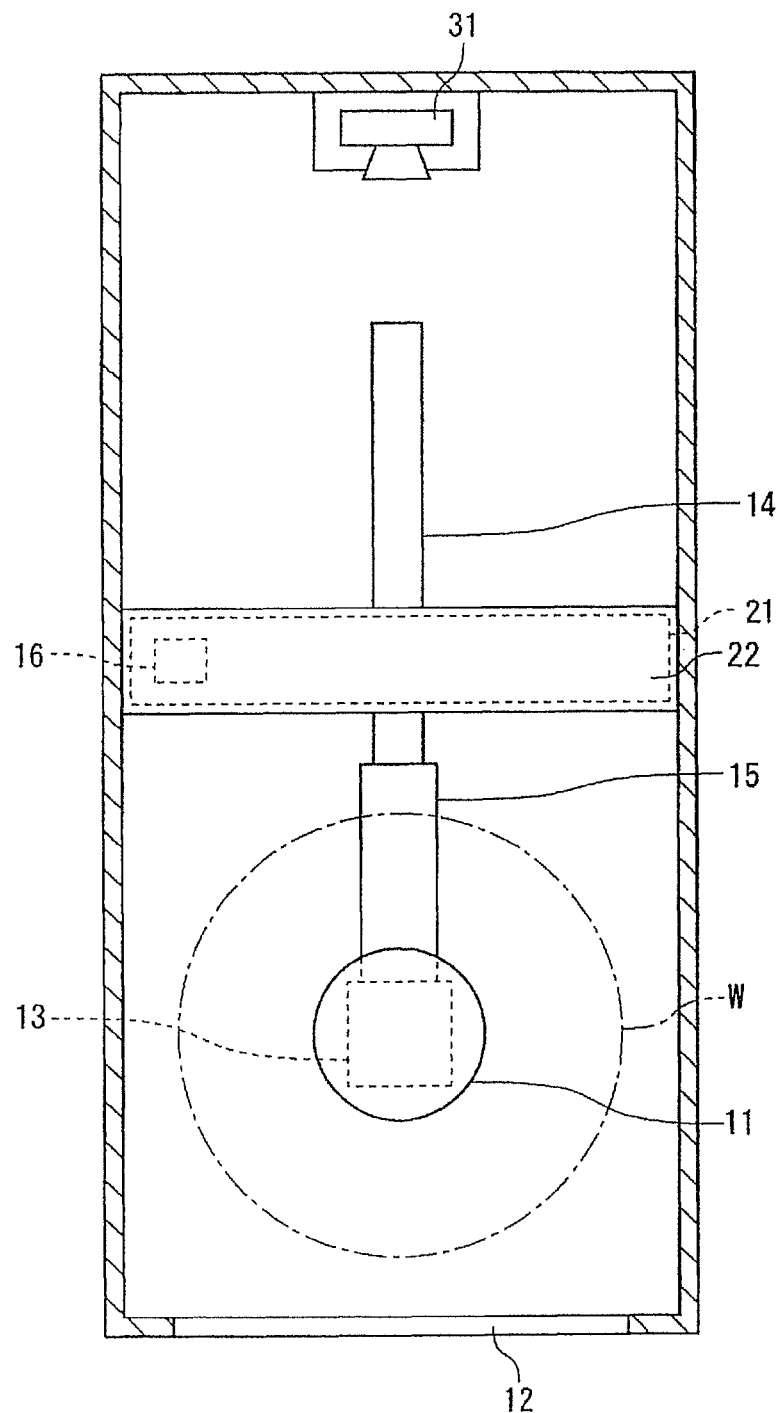
FIG. 16 is a horizontal cross sectional view of yet another substrate inspection apparatus.

The location where the reflector plate 16 is disposed is not limited to those shown in the foregoing embodiments. For example, as shown in FIG. 16, the reflector plate 16 may be located on a floor of the casing 10 below the illuminating unit 22 such that the reflector plate does not disturb the movement of the table 11 by the horizontal drive unit 13. However, in this case, in order to prevent a situation where a light reflected on the reflector plate 16 is reflected on the wafer W so that the light falls on the imaging device array 33 of the imaging camera 31 when the inspection mode is performed, the reflector plate 16 may be slightly inclined with respect to the horizontal plane, for example.

Figure 17:
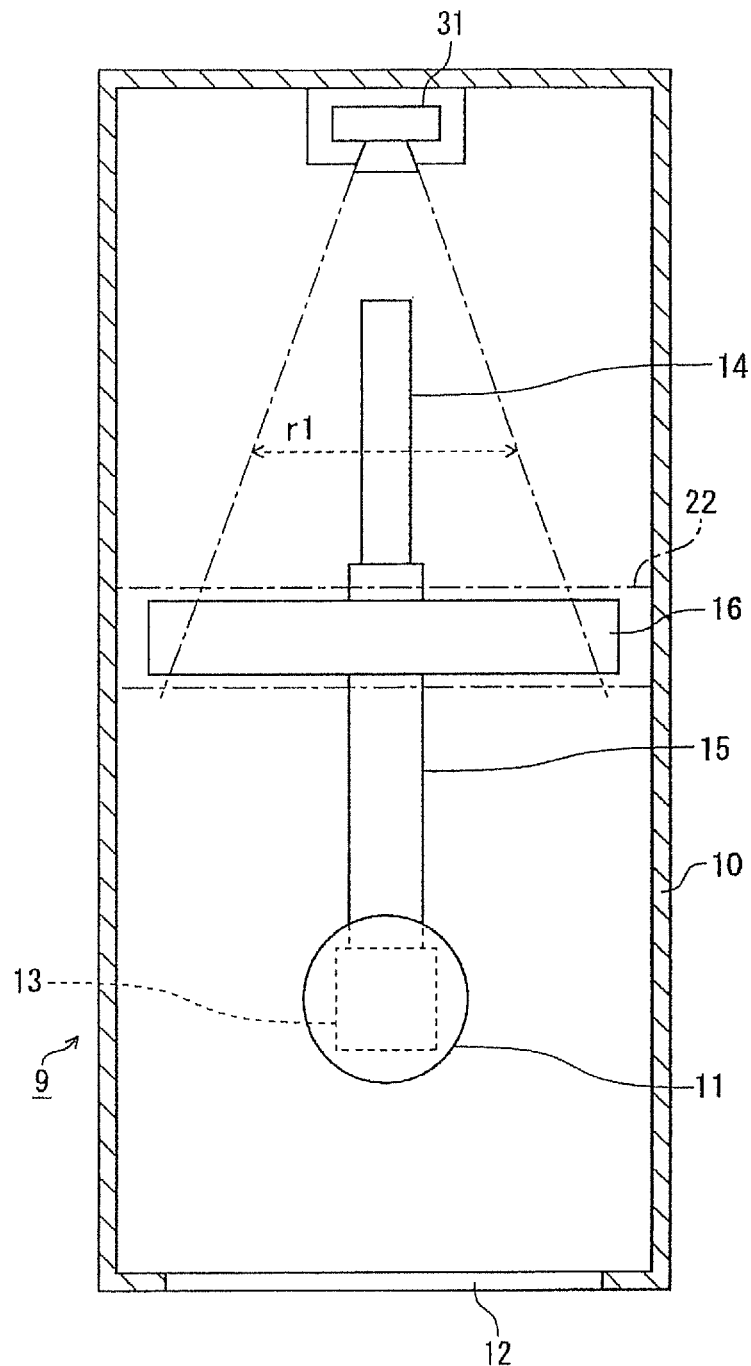
FIG. 17 is a horizontal cross sectional view of yet another substrate inspection apparatus.

FIG. 17 shows a yet another embodiment of the substrate inspection apparatus 9. In this embodiment, a laterally elongated reflector plate 16 is disposed on the cover 15, and all the imaging devices 30, which are laterally arranged, of the imaging device array 33 are concurrently illuminated by a light from the reflector plate 16. In this substrate inspection apparatus 9, brightness values obtained by a larger (as compared with the substrate inspection apparatus 1) number of imaging devices 30 (larger area of the imaging device array 33) can be sampled for judgment. In the judgment, it is judged whether or not the average of the sampled brightness values (or each of the sampled brightness values) falls within the allowable range. Therefore, even if the lowering degree of the illuminance of the illuminating unit 22 varies in the longitudinal direction of the illuminating unit 22, such a variation can be detected. It is thus possible to more reliably prevent a situation where the brightness of the image becomes lower than the allowable value.

In the forgoing embodiments, when the brightness value of the image is lower than the lower limit value in the maintenance mode, an alarm may be outputted instead of changing the correction value. Namely, in the above flow, after step S2 has been performed, step 8 may be performed without performing steps S3 to S6. In addition, the light-guiding member that guides a light emitted from the illuminating unit 22 to the imaging device array 33 is not limited to the reflector plate. For example, one end of an optical fiber may be located below the illuminating unit 22 and the other end of the optical fiber may be located to face the imaging camera 31, so that the light of the illuminating unit 22 is guided to the imaging device array 33.

A method of determining the target brightness value to be stored in the correction value setting data storage area 53 is described. A wafer on which a film such as a resist film is not formed is transferred into the substrate inspection apparatus 1. The substrate is imaged by the imaging camera 31. While watching an image of the wafer displayed on the display unit 45, the user manually varies the instruction value corresponding to the correction value used in the output correction unit 35, using the input unit 46, so as to specify the instruction value by which an image of a suitable brightness can be obtained. Immediately thereafter, the wafer is unloaded from the substrate inspection apparatus 1, and the reflector plate 16 is imaged by the imaging camera 31. Then, the brightness signals, which are obtained upon imaging of the reflector plate 16 and associated with the imaging device 30 on which the light from the reflector plate 16 falls, are amplified by the correction value corresponding to the specified instruction value, and the finally outputted from the control unit 4 is determined as the target brightness value.

In the foregoing embodiments, the maintenance mode may be performed upon the user's request or operation inputted by the input unit 46, for example, during a relatively long time interval between two adjacent production lots of wafers W during which wafers W are not transferred into the substrate inspection apparatus 1.

Alternatively, a host computer, which controls the transferring of the wafers in the substrate processing system, may transmit the transfer schedule or the estimated transfer time point of the two adjacent production lots of wafers to the control unit 4 of the substrate inspection apparatus 1. If the interval between the two production lots is longer than a threshold stored in the memory 44, the maintenance mode may be automatically initiated after completion of the inspection of the wafers W of the first production lot, and after completion of the maintenance mode, the operation mode may be automatically returned to the inspection mode to perform inspection of the wafers of the second production lot. The inspection mode program 51 and the maintenance mode program 52 may be configured for the above operations.

The substrate to be inspected by the substrate inspection apparatus is not limited to a semiconductor wafer, but may be a substrate of another type, such as a glass substrate for an LCD (liquid crystal display).

The invention claimed is:

1. A substrate inspection apparatus comprising:
a casing;
a table disposed in the casing for placement of a substrate thereon;
an illuminating unit provided to illuminate the substrate, placed on the table, with a light;
an imaging unit having an imaging device provided to image the substrate placed on the table illuminated with the light;
a mode selection unit configured to select one of an inspection mode in which an inspection of a substrate placed on the table is performed based on an image of the substrate obtained by the imaging unit, and a maintenance mode in which inspection of illuminance of the illuminating unit is performed;
a light-guiding member disposed in the casing to guide the light emitted from the illuminating unit to the imaging device;
a judging unit configured, upon execution of the maintenance mode, to judge whether or not a level of a brightness signal obtained by the imaging device falls within a predetermined allowable range when a light emitted from the illuminating unit falls on the imaging device via the light-guiding member;
an alarming unit configured to alarm, if the judging unit judges that the value of the brightness signal is out of the predetermined allowable range, that replacement of the illuminating unit is required; and
a control unit configured to receive a first estimated transfer time of substrates of a first production lot and a second estimated transfer time of substrates of a second production lot to be transferred immediately after the substrates of the first production lot, and configured to automatically make the inspection apparatus perform the maintenance mode after performing the inspection mode to the substrates of the first production lot, and thereafter perform the inspection mode to the substrates of the second production lot, if a time interval between the first estimated transfer time and the second estimated transfer time is longer than a predetermined threshold.

2. The substrate inspection apparatus according to claim 1, wherein the light-guiding member is provided in such a manner that the light emitted from the illuminating unit reaches the imaging device in the maintenance mode, while the light emitted from the illuminating unit does not reach the imaging device in the inspection mode.

3. The substrate inspection apparatus according to claim 2, wherein the light-guiding member is provided in such a manner that a light path, along which the light emitted from the illuminating unit travels from the light-guiding member to the imaging device when the maintenance mode is performed, is interrupted by a substrate placed on the table when the inspection mode is performed.

4. The substrate inspection apparatus according to claim 2, further comprising a drive mechanism configured to move the light-guiding member relative to the illuminating unit between a first position at which the light emitted from the illuminating unit is guided to the imaging device and a second position at which the light emitted from the illuminating unit is not guided to the imaging device.

5. The substrate inspection apparatus according to claim 1, wherein the light-guiding member comprises a reflector provided to reflect the light emitted from the illuminating unit.

6. A substrate inspection apparatus comprising:
a casing;
a table disposed in the casing for placement of a substrate thereon;
an illuminating unit provided to illuminate the substrate, placed on the table, with a light;
an imaging unit having an imaging device provided to image the substrate placed on the table illuminated with the light;
a mode selection unit configured to select one of an inspection mode in which an inspection of a substrate placed on the table is performed based on an image of the substrate obtained by the imaging unit, and a maintenance mode in which inspection of illuminance of the illuminating unit is performed;
a light-guiding member disposed in the casing to guide the light emitted from the illuminating unit to the imaging device;
an amplifying unit configured to amplify, at an adjustable amplification degree, a brightness signal outputted from the imaging device;
an amplification degree adjusting unit configured, upon execution of the maintenance mode, to adjust the amplification degree such that a level of the brightness signal outputted from the amplifying unit falls within a predetermined range when a light emitted from the illuminating unit falls on the imaging device via the light-guiding member; and
a control unit configured to receive a first estimated transfer time of substrates of a first production lot and a second estimated transfer time substrates of a second production lot to be transferred immediately after the substrates of the first production lot, and configured to automatically make the inspection apparatus perform the maintenance mode alter performing the inspection mode to the substrates of the first production lot, and thereafter perform the inspection mode to the substrates of the second production lot, if a time interval between the first estimated transfer time and the second estimated transfer time is longer than a predetermined threshold.

7. The substrate inspection apparatus according to claim 6, further comprising:
   a judging unit configured to judge whether or not the amplification degree adjusted by the amplification degree adjusting unit exceeds a predetermined allowable limit; and
   an alarming unit configured to alarm, if the judging unit judges that the amplification degree adjusted by the amplification degree adjusting unit exceeds the predetermined allowable limit, that replacement of the illuminating unit is required.

8. The substrate inspection apparatus according to claim 6, further comprising:
   a data storage unit configured to store values of the amplification degree adjusted by the amplification degree adjusting unit, and time periods from a time point when the illuminating unit is replaced to respective time points when the values of the amplification degree are adjusted; and
   a display unit configured to display the values of the amplification degree and the time periods, with the values of the amplification degree and the time periods being correlated with each other.

9. The substrate inspection apparatus according to claim 6, wherein the light-guiding member is provided in such a manner that the light emitted from the illuminating unit reaches the imaging device in the maintenance mode, while the light emitted from the illuminating unit does not reach the imaging device in the inspection mode.

10. The substrate inspection apparatus according to claim 9, wherein the light-guiding member is provided in such a manner that a light path, along which the light emitted from the illuminating unit travels from the light-guiding member to the imaging device when the maintenance mode is performed, is interrupted by a substrate placed on the table when the inspection mode is performed.

11. The substrate inspection apparatus according to claim 9, further comprising a drive mechanism configured to move the light-guiding member relative to the illuminating unit between a first position at which the light emitted from the illuminating unit is guided to the imaging device and a second position at which the light emitted from the illuminating unit is not guided to the imaging device.

12. The substrate inspection apparatus according to claim 6, wherein the light-guiding member comprises a reflector provided to reflect the light emitted from the illuminating unit.

13. A method of operating a substrate inspection apparatus, wherein said substrate inspection apparatus include a casing, a table disposed in the casing for placement of a substrate thereon, an illuminating unit provided to illuminate the substrate, placed on the table, with a light, and an imaging unit having an imaging device provided to image the substrate placed on the table illuminated with the light, and said substrate inspection apparatus is configured to allow inspection of a substrate based on an image, obtained by the imaging unit, of the substrate illuminated with the light of the illuminating unit, said method is performed under control of a computer, said method comprising:
   performing an inspection mode by which the substrate is inspected, the inspection mode including:
      imaging the substrate placed on the table illuminated with the light by means of the imaging device; and
      inspecting the substrate based on the image obtained by the imaging unit;
   performing a maintenance mode of the inspection apparatus, the maintenance mode including:
      guiding a light emitted from the illuminating unit to the imaging device via a light-guiding member disposed in the casing;
      judging whether or not a level of a brightness signal obtained by the imaging device falls within a predetermined allowable range when a light emitted from the illuminating unit falls on the imaging device via the light-guiding member;
      alarming, if it is judged that the value of the brightness signal is out of the predetermined allowable range, that replacement of the illuminating unit is required;
   acquiring a first estimated transfer time of substrates of a first production lot and a second estimated transfer time of substrates of a second production lot to be transferred immediately after the substrates of the first production lot;
   performing the inspection mode to the substrates of the first production lot;
   judging whether a time interval between the acquired first estimated transfer time and the second acquired estimated transfer time is longer than a predetermined threshold;
   performing the maintenance mode after performing the inspection mode to the substrates of the first production lot and before performing the inspection mode to the substrates of the second production lot, if the time interval between the first estimated transfer time and the second estimated transfer time is longer than a predetermined threshold; and
   performing the inspection mode to the substrates of the second production lot after performing the maintenance mode.

14. The method according to claim 13, further comprising:
   placing the light-guiding member in condition that the light-guiding member does not guide the light emitted from the illuminating unit to the imaging device, when a substrate is illuminated with the light emitted from the illuminating unit to be imaged by the imaging unit.

15. A method of operating a substrate inspection apparatus, wherein said substrate inspection apparatus include a casing, a table disposed in the casing for placement of a substrate thereon, an illuminating unit provided to illuminate the substrate, placed on the table, with a light, and an imaging unit having an imaging device provided to image the substrate placed on the table illuminated with the light, and said substrate inspection apparatus is configured to allow inspection of a substrate based on an image, obtained by the imaging unit, of the substrate illuminated with the light of the illuminating unit, said method is performed under control of a computer, said method comprising:
   performing an inspection mode by which the substrate is inspected, the inspection mode including:
      imaging the substrate placed on the table illuminated with the light by means of the imaging device; and
      inspecting the substrate based on the image obtained by the imaging unit;
   performing a maintenance mode of the inspection apparatus, the maintenance mode including:
      guiding a light emitted from the illuminating unit to the imaging device via a light-guiding member disposed in the casing;
      amplifying a brightness signal outputted from the imaging device at an amplification degree;

adjusting the amplification degree such that a level of the amplified brightness signal falls within a predetermined range; and acquiring a first estimated transfer time of substrates of a first production lot and a second estimated transfer time of substrates of a second production lot to be transferred immediately after the substrates of the first production lot;

performing the inspection mode to the substrates of the first production lot;

judging whether a time interval between the acquired first estimated transfer time and the second acquired estimated transfer time is longer than a predetermined threshold;

performing the maintenance mode after performing the inspection mode to the substrates of the first production lot and before performing the inspection mode to the substrates of the second production lot, if the time interval between the first estimated transfer time and the second estimated transfer time is longer than a predetermined threshold; and performing the inspection mode to the substrates of the second production lot after performing the maintenance mode.

16. The method according to claim 15, further comprising:
judging whether or not the adjusted amplification degree exceeds a predetermined allowable limit; and
alarming, if it is judged that the adjusted amplification degree exceeds the predetermined allowable limit, that replacement of the illuminating unit is required.

17. The method according to claim 15, further comprising:
displaying values of the amplification degree and time periods from a time point when the illuminating unit is replaced to respective time points when the values of the amplification degree are adjusted, with the values of the amplification degree and the time periods being correlated with each other.

18. The method according to claim 15, further comprising:
placing the light-guiding member in condition that the light-guiding member does not guide the light emitted from the illuminating unit to the imaging device, when a substrate is illuminated with the light emitted from the illuminating unit to be imaged by the imaging unit.

19. A non-transitory storage medium storing a computer program, wherein upon execution of the computer program, a control computer for controlling a substrate inspection apparatus makes the substrate inspection apparatus perform the method according to claim 13.

20. A non-transitory storage medium storing a computer program, wherein upon execution of the computer program, a control computer for controlling a substrate inspection apparatus makes the substrate inspection apparatus perform the method according to claim 15.

* * * * *